United States Patent
Olivier et al.

(10) Patent No.: US 9,475,157 B2
(45) Date of Patent: Oct. 25, 2016

(54) HOLDING NEEDLE COMPRISING GRIPPING CHEEKS

(71) Applicant: EMD Millipore Corporation, Billerica, MA (US)

(72) Inventors: Stephane Olivier, Rosheim (FR); Jerome Geyer, Wahlenheim (FR); Gerard Muller, Urmatt (FR)

(73) Assignee: EMD Millipore Corporation, Billerica, MA (US)

( * ) Notice: Subject to any disclaimer, the term of this patent is extended or adjusted under 35 U.S.C. 154(b) by 52 days.

(21) Appl. No.: 14/162,823

(22) Filed: Jan. 24, 2014

(65) Prior Publication Data

US 2014/0137386 A1    May 22, 2014

Related U.S. Application Data

(62) Division of application No. 11/258,478, filed on Oct. 25, 2005, now Pat. No. 8,668,673.

(30) Foreign Application Priority Data

Oct. 26, 2004  (FR) ...................................... 04 11416

(51) Int. Cl.
  *B23P 19/00*    (2006.01)
  *B23P 19/04*    (2006.01)
  (Continued)

(52) U.S. Cl.
  CPC ............ *B23P 19/04* (2013.01); *A61B 17/3421* (2013.01); *A61M 5/162* (2013.01);
  (Continued)

(58) Field of Classification Search
  CPC ..... B23P 19/002; B23P 19/04; A61M 5/162; A61M 5/158; A61M 25/06; A61M 25/065; A61M 2005/1623; Y10T 29/49947; Y10T 29/49895; Y10T 29/49897; Y10T 29/49899; Y10T 29/49892; Y10T 29/49826; A61B 17/3421; A61B 17/3417

USPC ....................................... 29/525.01, 463–466
See application file for complete search history.

(56) References Cited

U.S. PATENT DOCUMENTS 536,696 A * 4/1895 Hirsh ............................. 74/448
1,613,039 A * 1/1927 Peter ................... E21B 17/1085
                                                      175/325.5

(Continued)

FOREIGN PATENT DOCUMENTS

DE    4122476 A1 * 1/1993 ................ A61J 1/20
DE    19905644 A1    8/2000

(Continued)

OTHER PUBLICATIONS

DE 19905644 EPO English Machine translation; Fritz et al.; pp. 1-3.*

*Primary Examiner* — Christopher Besler
*Assistant Examiner* — Bayan Salone
(74) *Attorney, Agent, or Firm* — EMD Millipore Corporation (57) ABSTRACT

A take-off needle comprises a hollow lance having a distal end adapted to perform a insertion operation, said hollow lance being connected to at least one pipe provided with a spigot for it to be connected to a tube, and comprising a body for holding the hollow lance and pipe relative to each other such that the spigot projects from the holding body, said needle timber comprising two flanges held on respective sides of and spaced from the holding body by virtue of a spacer disposed between each flange and the holding body, said flanges extending in a longitudinal direction from the spigot to the vicinity of the proximal end of the hollow lance, the width of each flange being greater than the width of the portion of the holding body facing the flanges.

12 Claims, 7 Drawing Sheets

(51) Int. Cl.
*A61M 5/162* (2006.01)
*A61M 5/158* (2006.01)
*A61B 17/34* (2006.01)
*A61M 25/06* (2006.01)

(52) U.S. Cl.
CPC ......... *A61B 17/3417* (2013.01); *A61M 5/158* (2013.01); *A61M 25/06* (2013.01); *A61M 25/065* (2013.01); *A61M 2005/1623* (2013.01); *Y10T 29/49826* (2015.01); *Y10T 29/49892* (2015.01); *Y10T 29/49895* (2015.01); *Y10T 29/49897* (2015.01); *Y10T 29/49899* (2015.01); *Y10T 29/49947* (2015.01)

(56) References Cited

U.S. PATENT DOCUMENTS

| | | | | |
|---|---|---|---|---|
| 2,893,389 A * | 7/1959 | Nesset | ............ | 604/412 |
| 2,989,053 A * | 6/1961 | Hamilton | ............ | 604/274 |
| 3,429,700 A * | 2/1969 | Salter | ............ | B22F 7/062 29/463 |
| 3,757,031 A * | 9/1973 | Izraeli | ............ | H02G 15/113 138/155 |
| 3,759,180 A * | 9/1973 | Gibbons | ............ | B41K 1/56 101/405 |
| 3,893,445 A * | 7/1975 | Hofsess | ............ | 600/567 |
| 4,020,837 A * | 5/1977 | Larson | ............ | 604/411 |
| 4,292,405 A * | 9/1981 | Mascoli et al. | ............ | 435/31 |
| 4,351,900 A * | 9/1982 | Lemonnier | ............ | 435/31 |
| 4,411,661 A * | 10/1983 | Kersten | ............ | A61M 5/162 222/567 |
| 4,506,559 A * | 3/1985 | Francke et al. | ............ | 74/439 |
| 4,601,710 A * | 7/1986 | Moll | ............ | 604/164.12 |
| 4,723,955 A * | 2/1988 | Vaillancourt | ............ | 604/405 |
| 4,810,244 A * | 3/1989 | Allen | ............ | 604/44 |
| 4,822,351 A * | 4/1989 | Purcell | ............ | 604/411 |
| 4,834,744 A * | 5/1989 | Ritson | ............ | 604/411 |
| 4,857,068 A * | 8/1989 | Kahn | ............ | 604/405 |
| 5,030,205 A * | 7/1991 | Holdaway et al. | ............ | 604/164.02 |
| 5,057,058 A * | 10/1991 | Crudup | ............ | 474/95 |
| 5,098,394 A * | 3/1992 | Luther | ............ | 604/167.05 |
| 5,167,635 A * | 12/1992 | Haber et al. | ............ | 604/164.08 |
| 5,224,252 A * | 7/1993 | Baker et al. | ............ | 492/38 |
| 5,295,993 A * | 3/1994 | Green | ............ | 606/184 |
| 5,312,345 A * | 5/1994 | Cole | ............ | 604/110 |
| 5,318,585 A * | 6/1994 | Guy | ............ | A61B 17/3496 30/366 |
| 5,334,179 A * | 8/1994 | Poli et al. | ............ | 604/403 |
| 5,356,421 A * | 10/1994 | Castro | ............ | 606/185 |
| 5,372,582 A * | 12/1994 | Skrabal | ............ | A61M 25/0026 604/164.11 |
| 5,378,203 A * | 1/1995 | Baebel | ............ | 474/96 |
| 5,405,329 A * | 4/1995 | Durand | ............ | 604/164.01 |
| 5,407,807 A * | 4/1995 | Markus | ............ | 435/34 |
| 5,407,907 A | 4/1995 | Yamada et al. | | |
| 5,423,796 A * | 6/1995 | Shikhman | ............ | A61B 17/3494 604/164.08 |
| 5,445,630 A * | 8/1995 | Richmond | ............ | 604/411 |
| 5,486,190 A * | 1/1996 | Green | ............ | 606/184 |
| 5,549,564 A * | 8/1996 | Yoon | ............ | 604/164.12 |
| 5,571,133 A * | 11/1996 | Yoon | ............ | 606/185 |
| 5,603,706 A * | 2/1997 | Wyatt et al. | ............ | 604/539 |
| 5,658,260 A * | 8/1997 | Desecki et al. | ............ | 604/239 |
| 5,669,883 A * | 9/1997 | Scarfone et al. | ............ | 604/164.11 |
| 5,762,629 A * | 6/1998 | Kambin | ............ | 604/164.11 |
| 5,785,582 A * | 7/1998 | Stefanik et al. | ............ | 451/102 |
| D399,558 S * | 10/1998 | Guala et al. | ............ | D24/112 |
| 5,879,499 A * | 3/1999 | Corvi | ............ | 156/175 |
| 5,951,508 A * | 9/1999 | Van Driel | ............ | 604/6.15 |
| 5,971,950 A * | 10/1999 | Lopez et al. | ............ | 604/500 |
| 5,976,115 A * | 11/1999 | Parris et al. | ............ | 604/533 |
| 6,213,978 B1 * | 4/2001 | Voyten | ............ | 604/164.01 |
| 6,497,716 B1 * | 12/2002 | Green et al. | ............ | 606/185 |
| 6,634,076 B2 * | 10/2003 | Hjertman | ............ | F16L 25/0018 138/120 |
| 7,140,401 B2 * | 11/2006 | Wilcox et al. | ............ | 141/2 |
| 7,416,227 B1 * | 8/2008 | Earnest | ............ | F16L 55/1608 138/162 |
| 7,645,270 B2 * | 1/2010 | Geyer et al. | ............ | 604/411 |
| 8,668,673 B2 * | 3/2014 | Olivier et al. | ............ | 604/164.11 |
| 8,777,697 B2 * | 7/2014 | Deleris | ............ | 451/102 |
| 2002/0065486 A1 * | 5/2002 | Balbierz et al. | ............ | 604/164.02 |
| 2003/0028146 A1 * | 2/2003 | Aves | ............ | 604/164.06 |
| 2003/0069552 A1 * | 4/2003 | O'Keefe et al. | ............ | 604/278 |
| 2003/0204169 A1 * | 10/2003 | Howell et al. | ............ | 604/164.12 |
| 2003/0229330 A1 * | 12/2003 | Hickle | ............ | 604/411 |
| 2005/0033267 A1 * | 2/2005 | Decaria | ............ | 604/533 |
| 2006/0086750 A1 * | 4/2006 | Geyer et al. | ............ | 222/81 |
| 2006/0089047 A1 * | 4/2006 | Olivier et al. | ............ | 439/595 |
| 2008/0140054 A1 * | 6/2008 | Lee | ............ | 604/533 |

FOREIGN PATENT DOCUMENTS

| | | | | |
|---|---|---|---|---|
| DE | 19905644 C2 * | 3/2003 | | |
| EP | 0050459 A1 | 4/1982 | | |
| EP | 327519 A1 * | 8/1989 | ............ | A61J 5/00 |
| EP | 0591714 A1 | 4/1994 | | |
| EP | 1323403 A1 * | 7/2003 | ............ | A61J 1/20 |
| WO | WO 03051761 A2 * | 6/2003 | | |

* cited by examiner

HOLDING NEEDLE COMPRISING GRIPPING CHEEKS

CROSS-REFERENCE TO RELATED APPLICATIONS

The present application is a divisional patent application of U.S. patent application Ser. No. 11/258,478, filed on Oct. 25, 2005, which claims the benefit of priority of French Patent Application No. 0411416, filed on Oct. 26, 2004, the entire content of each of which is incorporated herein in its entirety.

The invention concerns the general field of take-off needles adapted to be inserted or pricked through an elastic wall or septum in order to take off liquid contained in a container closed by the wall/septum.

The invention more particularly concerns such a take-off needle which comprises a hollow lance generally formed from a fine steel tube provided at its distal end with a sharp insertion tip and connected to a pipe by its proximal end.

The tip is thus adapted to pass through said elastic wall to enable the liquid to flow in the hollow lance towards the pipe which comprises a spigot to which for example may be connected to a tube by which the taken-off liquid will be collected, for example, in a container.

Such needles generally comprise a polymer holding body molded over the proximal end of the hollow lance, the holding body forming an internal channel ensuring the flow of the liquid from the hollow lance to the spigot of the pipe. The holding both also enables the needle to be manipulated, in particular during the insertion operation.

Such needles are for example used to take off liquid from a bottle closed by a rubber bung. The spigot of the pipe is connected in advance to a tube leading to a container. Next the needle is inserted into the bung such that the distal end passes through the hung and reaches the medium to be taken-off, the user holding the needle by its holding body.

The liquid to be taken of then flows to the container, for example by gravity or with the help of a peristaltic pump or Use by the pressurization of the bottle containing the liquid.

Such needles may for example be referred to as "single" needles, that is to say that they only comprise a single hollow lance connected to just one pipe; or else they may be referred to as "double" needles, that is to say that they comprise a hollow lance of which the flow is divided into two at the holding body to go to two pipes for taking off the liquid simultaneously to two different containers.

These needles, whether single or double, may be vented, that is to say that they comprise a second hollow lance, of smaller diameter than the main hollow lance, which is inserted in the main hollow lance. This second hollow lance allows the progressive introduction of air into the bottle containing the liquid to be taken off as the liquid flows in the main hollow lance. Such a vented needle makes it possible to carry out take-off operations from a fluid-tight bottle.

Such take-off needles are known which are provided to be manipulated directly by the holding body. Although the form of the holding body is defined by its function, i.e. the connection of the hollow lance to the pipe, it may be grasped in the hand by the user to manipulate the take-off needle, in particular to perform the insertion operation, without touching the hollow lance.

The holding body comprises a cylindrical body extending from the hollow lance and in line therewith. The spigot of the pipe is connected to the cylindrical body so as to project transversely or obliquely. Several spigots may project from the cylindrical body.

The ergonomic quality of these needles is limited in that the hand of the user must adapt to the firms of the cylindrical body and of the spigot.

Other take-off needles are known which are adapted to be manipulated by their holding body, as set out above, and which further comprise a guard formed by a plate that is transverse to the cylindrical body of the holding body. The guard is disposed on the holding body in the vicinity of the junction between the cylindrical body and the hollow lance. During the insertion operation, the guard enables the fingers of the user to be held clear of the hollow lance by a physical barrier.

In particular, during the insertion operation, the guard forms a grip for the user's fingers which thereby avoid the risk of slipping onto the hollow lance.

The object of the invention is to improve this type of take-off needle by providing a needle which is more ergonomic.

To that end, the invention is directed to a take-off needle comprising a hollow lance having a distal end adapted to perform an insertion operation, said hollow lance being connected to at least one pipe provided with a spigot for it to be connected to a tube, and comprising a body for holding the hollow lance and pipe relative to each other such that the spigot projects from the holding body, said needle being characterized in that it further comprises two flanges held on respective sides of and spaced from the holding body by virtue of a spacer disposed between each flange and the holding body, said flanges extending in a longitudinal direction from the spigot to the vicinity of the proximal end of the hollow lance, the width of each flange being greater than the width of the portion of the holding body facing the flanges.

In such a take-off needle, the holding, body is, as it were, sandwiched between the two flanges. As these flange flanges transversely cover at least a portion of the holding body, it is much simpler for the user's hand to grasp the needle by both flanges than by the holding body.

According to a preferred feature, each of the flanges also extends between the spigot and the proximal end of the holding body, to be better held by the hand.

Each of the flanges may furthermore be arcuate so as to bowed towards the holding body.

The arcuate form of the flanges provides longitudinal centering of the user's hand with respect to the holding body. The hand intuitively locates around the arcuate flanges and in the concave form which they define.

For the same reasons, each of the flanges may also have a transverse curvature so as to present a rounded surface.

The needle according to the invention may further comprise the following advantageous features, either alone or in combination:

each of the flanges comprises a transverse guard at its distal end;
the spigot projects from the holding body between the two flanges;
the needle comprises two spigots projecting on respective sides of the holding body such that each of them projects between the two flanges, the spigot or spigots being thereby protected by the flanges, for example against the tubes connected to those spigots being accidentally pulled off;
the flanges are attached to the holding body via a shell the internal form of which mates with the external form of the holding body;
said shell comprises two half-shells each connected to one of the flanges;
said half-shells are identical and hermaphroditic.

The invention also relates to a method of manufacturing a take-off needle as presented above, said method comprising the following steps:

manufacturing an assembly comprising the holding body attached to the hollow lance and to the pipe;

mounting said half-shells onto the holding body.

Other features and advantages of the invention appear in the light of the following description of a preferred embodiment, given by way of non-limiting example, and made with reference to the accompanying drawings in which.

Figure 1:
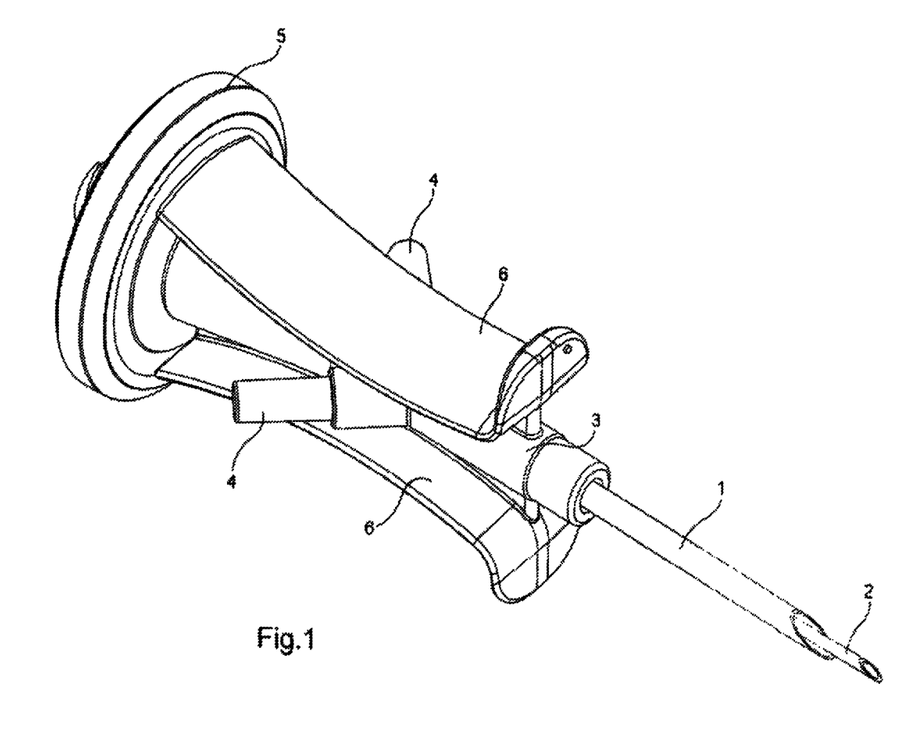
FIG. 1 is a perspective view of a double take-off needle according to the invention.
Figure 2:
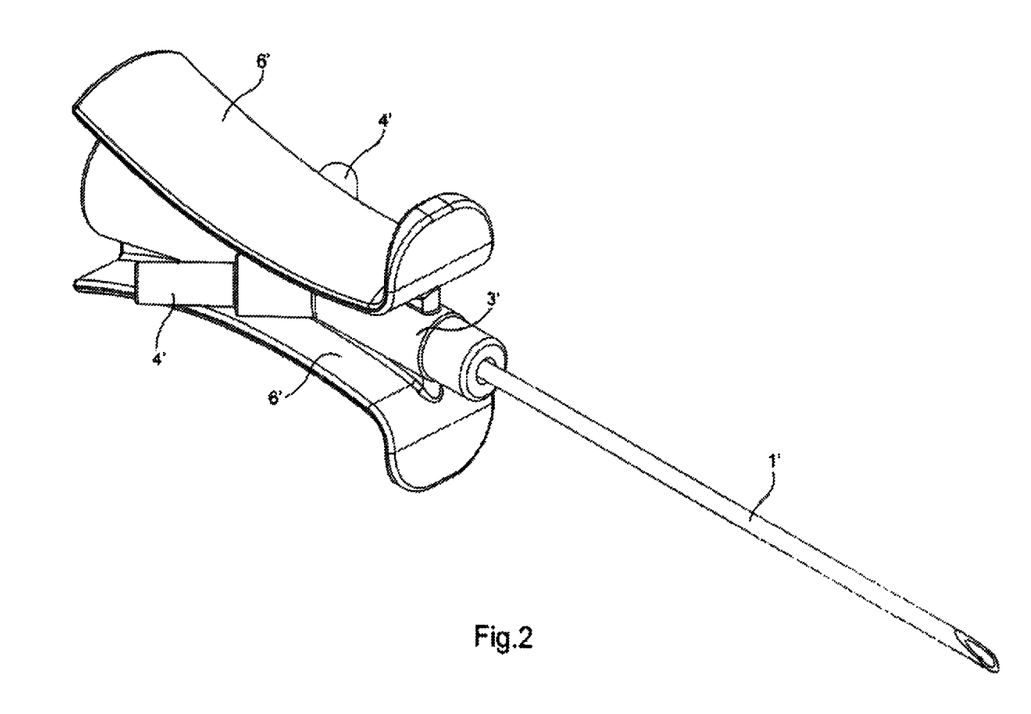
FIG. 2 is a perspective view of a single take-off needle according to the invention.

FIGS. 1 and 2 each represent a take-off needle in accordance with one embodiment of the invention.

FIG. 1 represents a double take-off needle comprising a main hollow lance 1 adapted for the passage of the liquid to take off a venting hollow lance 2 adapted to inject air into the container containing the liquid to be taken off, a holding body 3 defining an inner pipe which divides into two sub-pipes each provided with a spigot 4.

The liquid taken of flows in the main hollow lance 1 and is distributed by the spigots 4.

A tube may, for example, be connected to each of the spigots 4 in order to collect the liquid taken off in two different containers.

As regards the venting hollow lance 2, this passes through the inside of the holding body 3 to connect to a venting filter 5 which in the present example enables sterile air to be injected by the venting hollow lance 2.

This take-off needle further comprises two flanges 6 attached on respective sides of the holding body 3.

FIG. 2 on the other hand shows a single take-off needle. This needle comprises a single hollow lance 1' adapted for taking off liquid and does not include any part for injecting air.

As with the needle of FIG. 1, the needle of FIG. 2 comprises a holding body 3', two spigots 4' connected by an internal pipe of the holding body 3' to the hollow lance 1', and two flanges 6'.

The assembly formed by the holding body 3, 3', the spigots 4, 4' and the flanges 6, 6' is common to both embodiments of the take-off needle presented here in FIGS. 1 and 2. This assembly is represented in FIGS. 3 to 7 and will be described below using the numbering of the parts of FIG. 1, it being understood that the assembly represented in FIGS. 3 to 7 is also adapted to the embodiment of FIG. 2.

Figure 3:
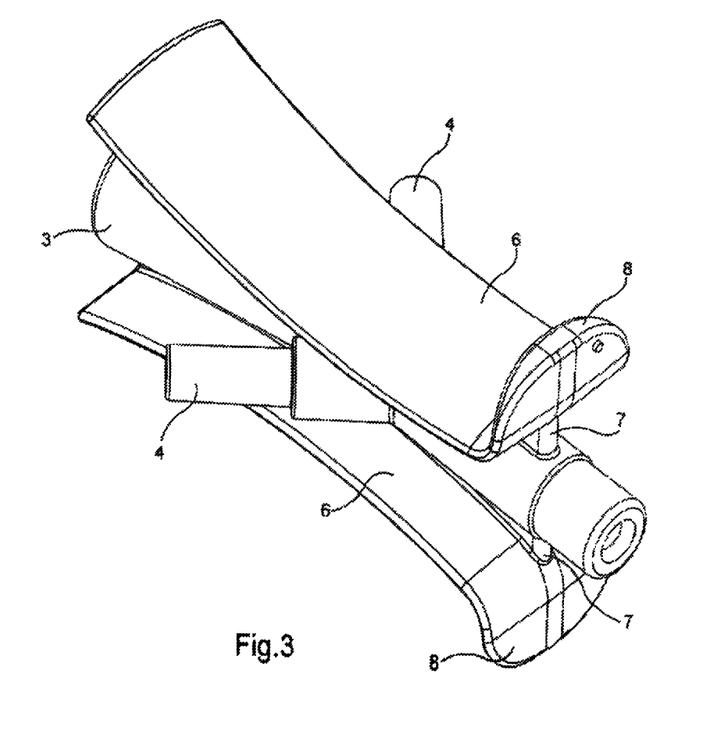
FIG. 3 is a perspective view of the assembly formed by the holding body provided with its two flanges, of the take-off needle of FIG. 1 or FIG. 2.
Figure 4:
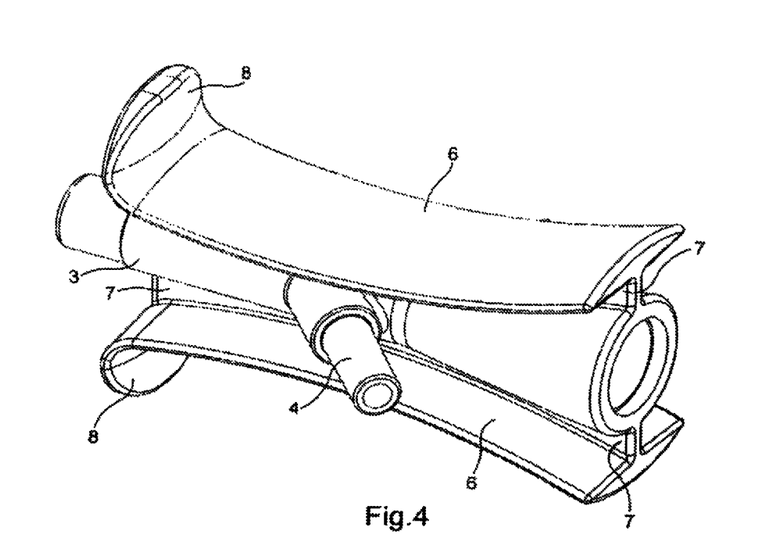
FIG. 4 is another perspective view of the assembly of FIG. 3.

FIGS. 3 and 4 are complementary perspective views to show the positioning of the flanges 6 with respect to the holding body 3.

Each flange 6 is connected onto the holding body 3 via a spacer 7 ensuring rigid fixing as well as spacing of the flanges 6 with respect to the holding body 3.

Figure 5:
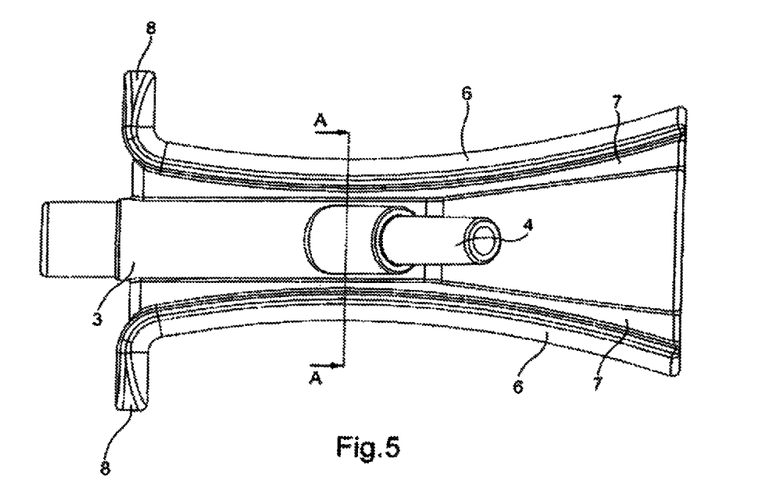
FIG. 5 is a side view of the assembly of FIG. 3.

As shown in FIG. 5, each spacer 7 mates with the form of the corresponding flange 6 and holding body 3 and fixes the flange 6 over practically the entirety of the length of the body 3.

Figure 6:
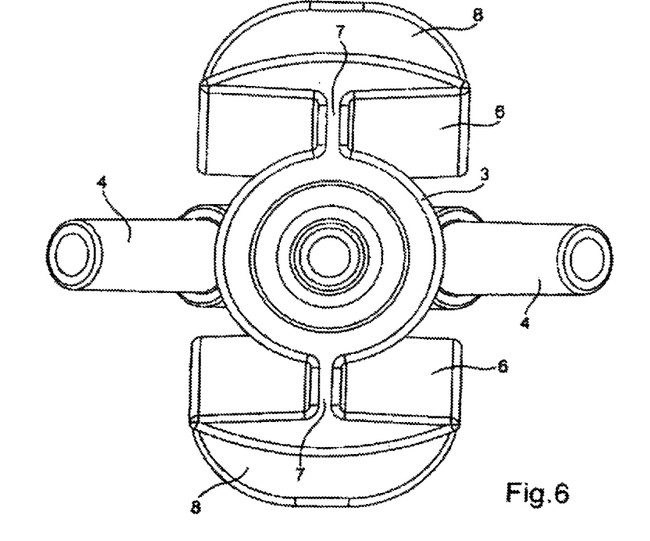
FIG. 6 is a view from the right of the assembly of FIG. 5.
Figure 7:
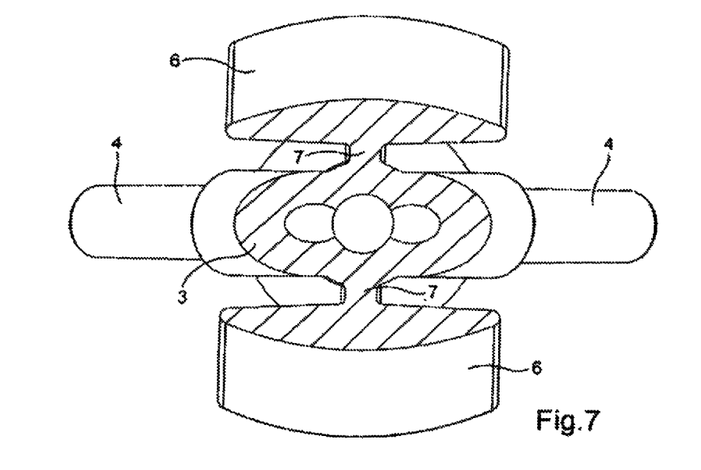
FIG. 7 is a view on section line A-A of FIG. 5.

The spacing between the flange 6 and the holding body 3 is also visible in FIG. 6 as well as on the cross-section in FIG. 7.

FIGS. 3 to 7, and more particularly FIG. 5, show that the flanges 6 are arcuate such that each of the flanges 6 is bowed towards the holding body 3. The flanges 6 consequently have a concave form with respect to the exterior adapted to facilitate grasping of the flanges 6 by the hand of the user.

The two flanges 6 are disposed on respective sides of the holding body 3 such that each spigot 4 projects between the two flanges 6 (see FIGS. 1 and 6).

With reference to FIG. 4 and FIGS. 6 and 7, each flange 6 furthermore has a radius of transverse curvature forming an outwardly directed rounded form.

This characteristic of a transverse rounded form combines with the arcuate form of the flanges 6 to ensure the user can grasp the needle well by the flanges 6.

Furthermore, FIGS. 3, 4 and 5 show that the flanges 6 comprise a guard 8 formed by a tab extending transversely of the corresponding flange 6.

The guard 8 provides a grip for the user's fingers during the insertion operation.

As regards the with of the flanges 6, FIG. 6 shows that each flange 6 has a width slightly greater than the maximum diameter of the holding body 3.

In the present example, the assembly of FIGS. 3 to 7 was produced with the following dimensions:

minimum diameter of the holding body 3: approximately 7 mm maximum diameter of the holding body 3: approximately 13 mm thickness of the spacer 7: approximately 1 to 2 mm length of the flanges 6: approximately 40 to 50 mm minimum separation between the outer surfaces of the flanges 6 (in the proximity of the section line A-A of FIG. 5): approximately 15 min radius of curvature of the arcuate form of the flanges 6: approximately 70 to 80 mm radius of curvature of the transverse rounded form of the flanges 6: approximately 15 to 20 mm width of the flanges approximately 15 mm.

Figure 8:
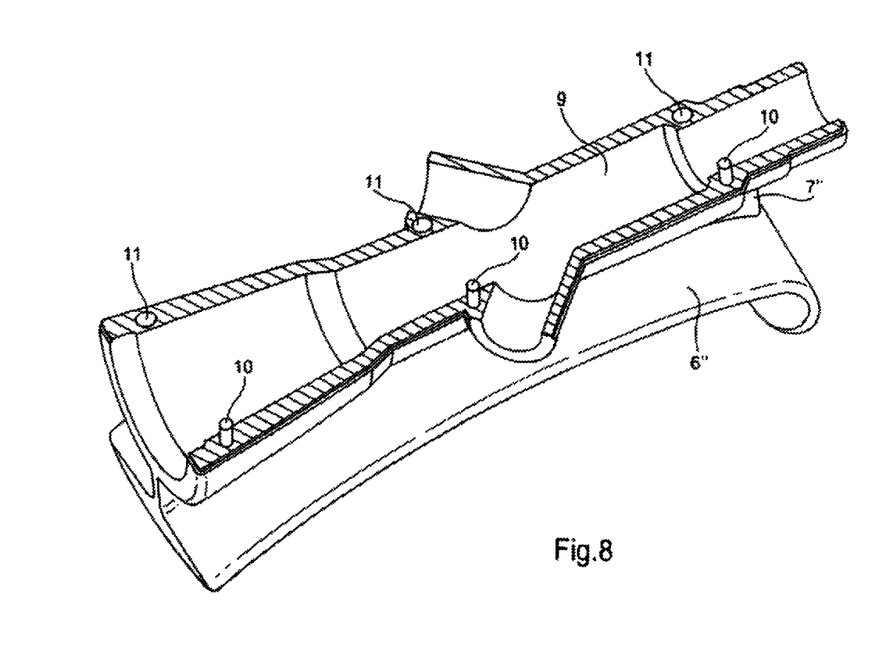
FIG. 8 is a perspective view of a half-shell provided with a flange.
Figure 9:
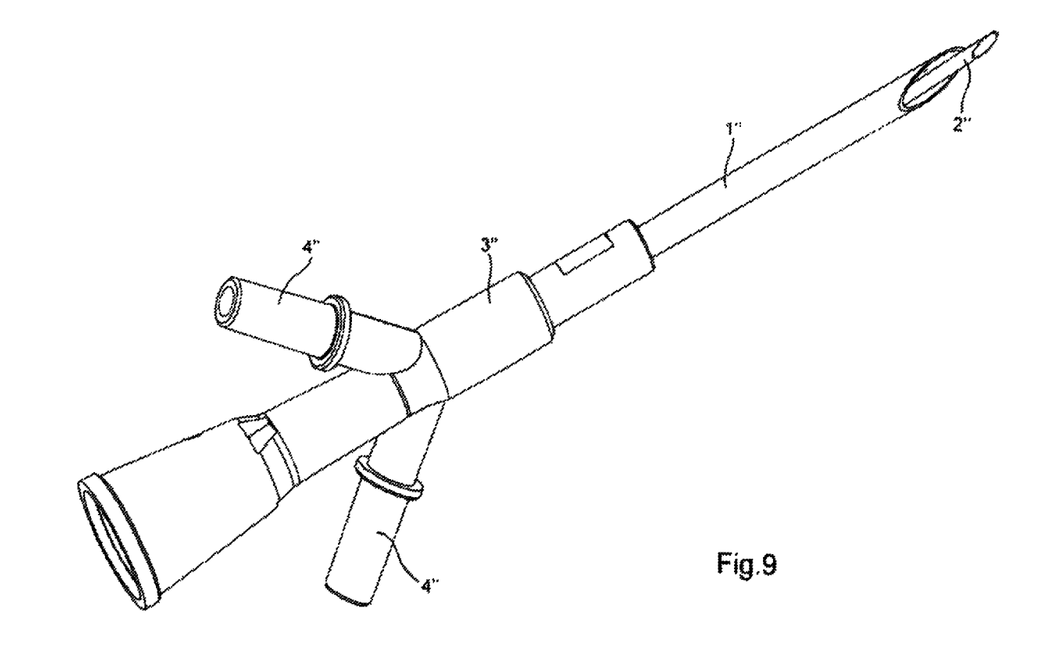
FIG. 9 is a perspective view of a take-off needle comprising a holding body onto which can be added two half-shells in accordance with that of FIG. 8.

With reference to FIGS. 8 and 9, an alternative embodiment of the invention will now be described. The parts of the same nature as in the embodiments of FIGS. 1 to 7 will bear the same number in FIGS. 8 and 9 followed by a "second" sign (").

In this embodiment, the flanges 6" are not directly fixed to the holding, body 3". More particularly they are each fixed to a half-shell 9 which is then attached to the holding body 3".

On producing such a needle, a first step consists of producing an assembly formed from a holding body 3", provided with the hollow lances 1", 2" and the spigots 4" (see FIG. 9).

Two other parts each in accordance with FIG. 8 and identical to each other are next produced. These parts each comprise a flange 6".

With reference to FIG. 8, a flange 6" similar to the one described previously is fixed by a spacer 7" to a half-shell 9 which is hermaphroditic in that it is a part comprising an axis of symmetry and comprising pins 10 on one of the lateral edges and corresponding holes 11 on the other of its lateral edges.

The internal volume of the half-shell 9 reproduces the exterior form of the holding body 3" and of the spigots 4".

Two parts in accordance with FIG. 8 may be assembled together, the pins 10 of one entering the holes 11 of the other. This assembly is made on the holding body 3" such that the latter is trapped between the two half-shells 9.

Once the assembly has been completed, a take-off needle provided with two flanges 6" rigidly attached to the holding body 3" is produced.

Variant embodiments of the take-off needle may be envisaged without departing from the scope of the invention. For example, the hollow lances and the spigots may have a different configuration, it being possible for example for the needle to comprise only a single spigot.

The invention claimed is:

1. A method of manufacturing a take-off needle comprising the steps:
    manufacturing an assembly comprising a holding body attached to one or more hollow lances and to one or more spigots, wherein each spigot is connected to and projecting from the holding body in a direction selected from the group consisting of transversely and obliquely;
    forming two half shells to fit over the assembly, wherein the two half shells extend between the one or more spigots to a proximal end of the holding body, each half shell having an internal form which mates with an external form of the holding body, wherein the two half shells together mate with the external form of the holding body, and extend in a longitudinal direction from at least the one or more spigots to a vicinity of a proximal end of the one or more hollow lances; and
    mounting said half-shells onto the holding body.

2. A method of manufacturing a take-off needle comprising the steps:
    manufacturing an assembly comprising a holding body attached to one or more hollow lances and to two spigots, wherein each spigot is connected to and projecting from the holding body in a direction selected from the group consisting of transversely and obliquely;
    forming two half shells to fit over the assembly, wherein the two half shells extend between the two spigots to a proximal end of the holding body, each half shell having an internal form which mates with an external form of the holding body, wherein the two half shells together mate with the external form of the holding body, and extend in a longitudinal direction from the two spigots to a vicinity of a proximal end of the one or more hollow lances;
    the half shells each have an outer surface, each outer surface having a flange fixed to it by a spacer wherein each of the flanges is arcuate so as to be bowed towards the holding body, and
    mounting said half-shells onto the holding body so that the spigots project from between the flanges.

3. The method of claim 1 wherein the one or more hollow lances is a double take-off needle.

4. The method of claim 1 wherein the one or more hollow lances is a double take-off needle comprising a main hollow lance adapted for the passage of liquid to be taken off and a venting hollow lance adapted to inject air into a container containing the liquid to be taken off.

5. The method of claim 2 wherein the one or more hollow lances is a double take-off needle.

6. The method of claim 2 wherein the one or more hollow lances is a double take-off needle comprising a main hollow lance adapted for the passage of liquid to be taken off of a container containing the liquid and a venting hollow lance adapted to inject air into the container containing the liquid to be taken off.

7. A method of forming a dual take-off needle comprising the steps of
    producing an assembly formed from a holding body having two hollow lances, a first main hollow lance adapted for the passage of liquid to be taken off of a container containing the liquid and a second venting hollow lance adapted to inject air into the container containing the liquid to be taken off and two spigots extending from the holding body, wherein each spigot is connected to and projecting from the holding body in a direction selected from the group consisting of transversely and obliquely;
    producing two half shells to fit over the assembly, wherein the two half shells extend between the two spigots to a proximal end of the holding body, each half shell having a flange fixed to the respective half shell by a spacer, each half shell having an internal surface which mates with an exterior surface of the assembly; and
    attaching the half shells to the exterior surface of the assembly.

8. The method of claim 7 wherein each half-shell is hermaphroditic in that it is a part comprising an axis of symmetry.

9. The method of claim 7 wherein each half-shell is hermaphroditic in that it is a part comprising an axis of symmetry and further comprising pins on one of its lateral edges and corresponding holes on the other of its lateral edges.

10. The method of claim 7 wherein each half-shell is hermaphroditic in that it is a part comprising an axis of symmetry and further comprising pins on one of its lateral edges and corresponding holes on the other of its lateral edges and the half shells are attached to the assembly by having the pins of one half shell entering the holes of the other half shell.

11. The method of claim 1 wherein each half-shell is hermaphroditic in that it is a part comprising an axis of symmetry and further comprising pins on one of its lateral edges and corresponding holes on the other of its lateral edges and the half shells are attached to the assembly by having the pins of one half shell entering the holes of the other half shell.

12. The method of claim 2 wherein each half-shell is hermaphroditic in that it is a part comprising an axis of symmetry and further comprising pins on one of its lateral edges and corresponding holes on the other of its lateral edges and the half shells are attached to the assembly by having the pins of one half shell entering the holes of the other half shell.

* * * * *